US00PP37813P3

(12) United States Plant Patent
Schoone

(10) Patent No.: US PP37,813 P3
(45) Date of Patent: Oct. 20, 2026

(54) ***PHALAENOPSIS* PLANT NAMED 'Vanity Bonfire'**

(50) Latin Name: *Phalaenopsis hybrida*
Varietal Denomination: Vanity Bonfire

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/631,779

(22) Filed: Mar. 27, 2026

(65) Prior Publication Data

US 2026/0305508 P1 Oct. 1, 2026

Related U.S. Application Data

(60) Provisional application No. 63/781,328, filed on Mar. 31, 2025.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan Mccormick Ewoldt
(74) *Attorney, Agent, or Firm* — C. Anne Whealy

(57) ABSTRACT

A new and distinct cultivar of *Phalaenopsis* plant named 'Vanity Bonfire', characterized by its upright plant habit; moderately vigorous growth habit; mostly horizontal leaves; freely flowering habit with typically two inflorescences developing per plant, each inflorescence with numerous flowers; flowers with purplish pink-colored petals and sepals that are densely covered with purplish red-colored venation and spots; and good postproduction longevity.

2 Drawing Sheets

Figure 1:
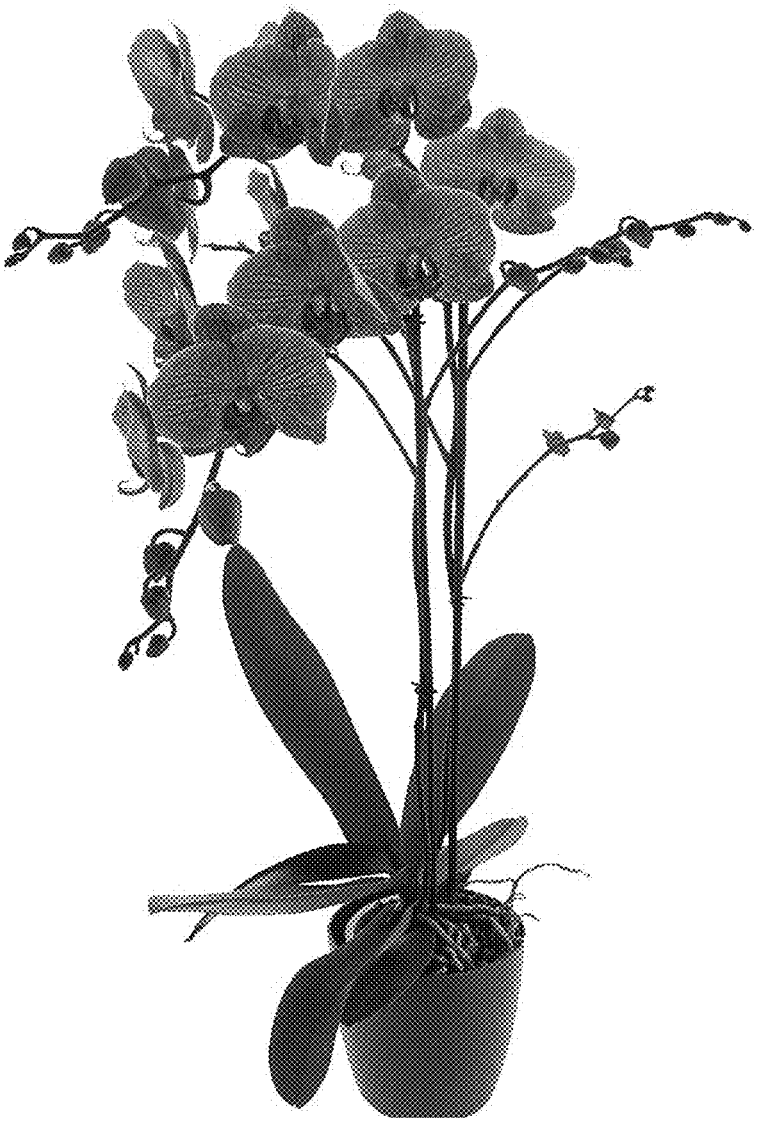

Botanical designation: *Phalaenopsis hybrida.*
Cultivar denomination: 'VANITY BONFIRE'.

CROSS-REFERENCED TO CLOSELY-RELATED APPLICATIONS:

A European Community Plant Breeder's Rights application for the instant plant was filed by the Applicant/Assignee, Floricultura B.V. of Heemskerk, The Netherlands on Apr. 28, 2025, application number 2025/0890. Foreign priority is not claimed to this application.

BACKGROUND OF THE INVENTION

The present invention relates to a new and distinct cultivar of *Phalaenopsis* plant, botanically known as *Phalaenopsis hybrida,* and hereinafter referred to by the name 'Vanity Bonfire'.

The new *Phalaenopsis* plant is a product of a planned breeding program conducted by the Inventor in Heemskerk and Assendelft, The Netherlands. The objective of the breeding program is to develop new fast-growing and freely flowering *Phalaenopsis* plants with good leaf shape and strength and flowers with unique and attractive patterns and coloration.

The new *Phalaenopsis* plant originated from a cross-pollination on Oct. 7, 2014 in Heemskerk, The Netherlands of a proprietary selection of *Phalaenopsis hybrida* identified as code number 1026899, not patented, as the female, or seed, parent with a proprietary selection of *Phalaenopsis hybrida* identified as code number 1026903, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in July 2021.

Asexual reproduction of the new *Phalaenopsis* plant by in vitro meristem propagation in a controlled environment in Assendelft, The Netherlands since August 2022 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Vanity Bonfire'. These characteristics in combination distinguish 'Vanity Bonfire' as a new and distinct *Phalaenopsis* plant:

1. Upright plant habit.
2. Moderately vigorous growth habit.
3. Mostly horizontal leaves.
4. Freely flowering habit with typically two inflorescences developing per plant, each inflorescence with numerous flowers.
5. Flowers with purplish pink-colored petals and sepals that are densely covered with purplish red-colored venation and spots.
6. Good postproduction longevity.

Plants of the new *Phalaenopsis* can be compared to plants of the female parent selection. Plants of the new *Phalaen-*

*opsis* differ primarily from plants of the female parent selection in petal color as petals of plants of the new *Phalaenopsis* are purplish pink in color and densely covered with purplish red-colored venation and spots whereas petals of plants of the female parent selection are dark purplish red without discernible venation and spots.

Plants of the new *Phalaenopsis* can be compared to plants of the male parent selection. Plants of the new *Phalaenopsis* differ primarily from plants of the female parent selection in petal color as the venation pattern of petals of plants of the new *Phalaenopsis* is denser than the venation pattern of petals of plants of the male parent selection which is sparse.

Plants of the new *Phalaenopsis* can be compared to plants of x *Phalaenopsis hybrida* 'Tropic Wonderland', not patented. In side-by-side comparisons, plants of the new *Phalaenopsis* differ primarily from plants of 'Tropic Wonderland' in the following characteristics:

1. Petals of plants of the new *Phalaenopsis* are not as separate as petals of plants of 'Tropic Wonderland'.
2. Petals of plants of the new *Phalaenopsis* are purplish pink in color and densely covered with purplish red-colored venation and spots whereas petals of plants of 'Tropic Wonderland' are creamy pink in color and sparsely to moderately covered with contrasting venation.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Vanity Bonfire' grown in a container.

Figure 2:
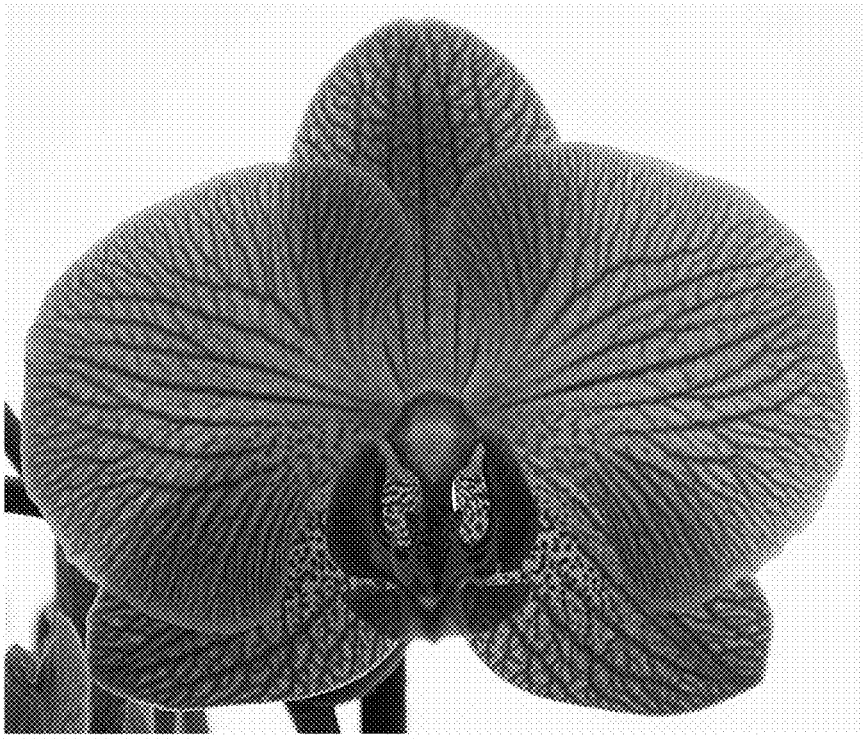

The photograph on the second sheet (FIG. 2) is a close-up view of a typical flower of 'Vanity Bonfire'.

DETAILED BOTANICAL DESCRIPTION

The aforementioned photographs and following observations and measurements describe plants grown during the summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Vanity Bonfire'.

Parentage:

*Female, or seed, parent*.—Proprietary breeding selection of *Phalaenopsis hybrida* identified as code number 1026899, not patented.

*Male, or pollen, parent*.—Proprietary breeding selection of *Phalaenopsis hybrida* identified as code number 1026903, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane*.—About 17 cm.

*Plant height, substrate level to top of floral plane*.—About 50.1 cm.

*Plant diameter or spread*.—About 44.3 cm.

Leaf description:

*Arrangement and quantity*.—Distichous, simple; sessile; about five to seven fully-developed leaves per plant.

*Length*.—About 22.6 cm.

*Width*.—About 5.7 cm.

*Aspect*.—Mostly horizontal.

*Shape*.—Oblanceolate to narrowly elliptic; moderately carinate.

*Apex*.—Unequal broadly acute.

*Base*.—Sheathed. Sheath length: About 1.7 cm. Sheath width: About 1.5 cm. Sheath color, upper and lower surfaces: Close to a blend of N186B and N186C.

*Margin*.—Entire.

*Texture and luster, upper and lower surfaces*.—Smooth, glabrous; slightly glossy.

*Venation pattern*.—Camptodromous.

*Color*.—Developing leaves, upper surface: Close to NN137A; towards the margins, tinged with close to 147A. Developing leaves, lower surface: Close to 146A strongly tinged with close to N186C. Fully expanded leaves, upper surface: Close to NN137B; venation, close to 147A. Fully expanded leaves, lower surface: Close to a blend of 146A and 146B; towards the margins, moderately to strongly tinged with close to 200A; venation, close to 146A.

Inflorescence description:

*Appearance and flowering habit*.—Showy zygomorphic flowers arranged on axillary simple or branched racemes; typically two inflorescences develop per plant; each inflorescence with about 22 flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about five weeks on the plant; flowers not persistent.

*Inflorescence length* (*lowermost flower to inflorescence apex*).—About 43.4 cm.

*Inflorescence width*.—About 63.7 cm.

*Flower buds* (*about one week before flower opening*).—Height: About 2.1 cm. Diameter: About 1.7 cm. Shape: Broadly ovoid. Color: Close to 177B and 177C; lower surface, tinged with close to 184B; venation, close to 183A.

*Flower size*.—About 7.5 cm (vertical) by 8.8 cm (horizontal).

*Flower depth*.—About 3.4 cm.

*Petals, quantity and arrangement*.—Three, two lateral petals and one center petal transformed into a labellum.

*Lateral petals*.—Length: About 4 cm. Width: About 5.3 cm. Shape: Reniform to close to broadly lunate; not imbricate. Apex: Obtuse. Margin: Entire; not undulate. Texture and luster, upper and lower surfaces: Smooth, glabrous; moderately velvety; matte. Color: When opening, upper surface: Close to 179C; towards the base, close to 162C and 162D; venation, close to 187D. When opening, lower surface: Close to 182B to 182D; towards the base, fading to close to 162C and 162D; venation, close to 184C and 184D. Fully opened, upper surface: Close to a blend of 70D and 73B; towards the base, fading to close to 158D; venation, close to 71A and 71B; colors do not change with subsequent development. Fully opened, lower surface: Close to N74D; towards the base, fading to close to 76D; venation, close to 70B; colors do not change with subsequent development.

*Labella*.—Appearance: Three-parted with two lateral lobes and a central lobe. Length, lateral lobes: About 2 cm. Width, lateral lobes: About 1.4 cm. Length, central lobe: About 2.3 cm. Width, central lobe: About 0.6 cm to 2 cm. Length, cirrhose apices: About 1.3 cm. Shape, lateral lobes: Broadly obovate. Shape, central lobe: Narrowly deltoid with a slightly elongated apex. Apex, lateral lobes: Obtuse. Apex, central lobe: Minutely bluntly acute with two cirrhose apices curled upwards and backwards. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 6 mm in width and about 6 mm in height. Color, lateral lobes: When opening and fully opened, upper surface: Close to 70A and 70B; towards the base, close to NN155D; venation, close to 61A. When opening and fully opened, lower surface: Close to 155C; towards the apex, close to 84C and at the apex, flushed with close to N78D; lower margins, close to 183D. Color, central lobe: When opening, upper surface: Close to 60C; towards the base, close to 160C and at the base, close to 185B; blotch, close to N155C; venation, close to 61A and 61B; cirrhose apices, close to 60C. When opening, lower surface: Close to 186C; towards the margins, close to 187D; center, close to 158C; at the base, close to 158B, blotch, close to 184C; venation, close to 64B; cirrhose apices, proximally, close to 186C and distally, close to 187D. Fully opened, upper surface: Close to 60C; apical margins, close to 182A; towards the base, close to 160C and at the base, close to 185A; blotch, close to 70B; venation, close to 61A and 61B; cirrhose apices, close to 60C. Fully opened, lower surface: Close to 186C; towards the margins, close to 187D and apical margins, close to 176C; center, close to 158C; at the base, close to 158B, blotch, close to 184C; venation, close to 64B; cirrhose apices, proximally, close to 186C and distally, close to 187D. Color, callosities: When developing: Close to N155B; towards the apices, close to 13B; fine dots and stripes, close to 183B. Fully developed: Close to 12D; towards the apex, close to 13A; fine dots and stripes, close to 183B.

*Sepals*.—Quantity and arrangement: Three, one upper dorsal sepal and two lower lateral sepals. Length, dorsal and lateral sepals: About 4.4 cm. Width, dorsal and lateral sepals: About 3.2 cm. Shape, dorsal sepal: Ovate to elliptic. Shape, lateral sepals: Ovate. Apex, dorsal sepal: Obtuse. Apex, lateral sepals: Broadly and bluntly acute. Base, dorsal and lateral sepals: Cuneate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to 179C; towards the base, close to 162B; venation, close to 187C. When opening, lower surface: Close to 177C and 177D; towards the margins and apex, close to 182B; venation, close to 184C. Fully opened, upper surface: Close to 186C; towards the base, fading to close to 158B; venation, close to 64A and 64B. Fully opened, lower surface: Close to 185D; towards the margins and apex, close to 186D; venation, close to 64B. Color, lateral sepals: When opening, upper surface: Close to 161A; towards the base, close to 160A. When opening, lower surface: Close to 182B and 182C; venation, close to 178A. Fully opened, upper surface: Close to 158B; towards the base, fading to close to 160A; venation, close to 64A, 59A and 59B. Fully opened, lower surface: Close to 186B and 186C; venation, close to 71B and 186A.

*Peduncles*.—Length: About 63.7 cm. Diameter: About 5.5 mm. Strength: Strong. Aspect: Upright to outwardly arching. Texture and luster: Smooth, glabrous; matte. Color: Close to N189A and N189B; densely covered with fine dots, close to 147C.

*Pedicels*.—Length: About 4.3 cm. Diameter: About 3 mm. Strength: Moderately strong. Aspect: About 65° from peduncle axis. Texture and luster: Smooth, glabrous; matte. Color: Close to a blend of 197A and 199A; proximal end, strongly tinged with close to 183B.

*Reproductive organs*.—Androecium: Column length: About 1 cm. Column width: About 5.5 mm. Column color: Close to a blend of N78D and NN78D; at the base, close to N78A and at the apex, closer to NN155D. Pollinia quantity: Two. Pollinia diameter (per two pollinia): About 2.5 mm. Pollinia color: Close to 23A. Gynoecium: Stigma length: About 3 mm. Stigma width: About 4 mm. Stigma shape: Reniform. Stigma color: Close to N155A. Ovary length: About 1 cm. Ovary diameter: About 1 mm.

Ovary color: Close to 145D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Vanity Bonfire' as herein illustrated and described.

* * * * *